US006576638B1

(12) United States Patent
Pompei et al.

(10) Patent No.: US 6,576,638 B1
(45) Date of Patent: Jun. 10, 2003

(54) USE OF SUBSTANCE P ANTAGONISTS IN THE TREATMENT OF THE ADENOCARCINOMAS

(75) Inventors: Pierluigi Pompei, Camerino (IT); Maurizio Massi, Camerino (IT); Massimo Nabissi, Tolentino (IT); Pier Luigi Sparapani, Camerino (IT)

(73) Assignee: Biopolis S.p.A., Siena (IT)

( * ) Notice: Subject to any disclaimer, the term of this patent is extended or adjusted under 35 U.S.C. 154(b) by 0 days.

(21) Appl. No.: 10/030,305

(22) PCT Filed: Jul. 5, 2000

(86) PCT No.: PCT/EP00/06309

§ 371 (c)(1),
(2), (4) Date: May 13, 2002

(87) PCT Pub. No.: WO01/01922

PCT Pub. Date: Jan. 11, 2001

(30) Foreign Application Priority Data

Jul. 5, 1999 (IT) ........................................ RM99A0426

(51) Int. Cl.$^7$ .......................... A61K 38/00; A61K 31/44
(52) U.S. Cl. .......................... 514/278; 514/34; 514/326; 514/353; 514/338; 514/416; 514/419; 514/254.01; 514/15
(58) Field of Search ................................ 514/278, 326, 514/353, 338, 416, 15, 254.01, 34, 419

(56) References Cited

U.S. PATENT DOCUMENTS 5,716,979 A    2/1998   Horwell et al.

FOREIGN PATENT DOCUMENTS

| WO | EP 0 659 409 | 6/1995 |
| WO | EP 0 773 026 | 5/1997 |
| WO | EP 0 835 662 | 4/1998 |

OTHER PUBLICATIONS

Hennig, I. M. et al., *Substance–P receptors in human primary neoplasms: Tumoral and vascular localization, Intl. Journ. of Cancer,* vol. 61, pp. 786–792, 1995.

Kucharczyk, N., *Tachykinin Antagonists in Development, Expert Opinion on Investigational Drugs,* vol. 4, No. 4, pp. 299–311, 1995.

M.A. Cascieri et al. *Characterization of the Binding of a Potent, Selective, Radioiodinated Antagonist to the Human Neurokin–1 Receptor.* Molecular Pharmacology vol. 42, pp. 458–463.

R. Cirillo et al. *Pharmacology of the peptidomimetic, MEN 11149, a new potent, selective and orally effective tachykinin $NK_1$ receptor antagonist.* European Journal Of Pharmacology vol.341, pp. 201–209 (1998).

M.C. Desai et al. *Discovery of a Potent Substance P Antagonist: Recognition of the Key Molecular Determinant.* J. Med. Chem vol. 35, pp. 4911–4913 (1992).

X. Emonds–Alt et al. *In vitro and in vivo biological activies of SR140333, a novel potent non–peptide tachykinin $NK_1$ receptor antagonist.* European Journal Of Pharmacology vol. 250, pp. 403–413 (1993).

S. Evangelista et al. *Colitis Induced by Acetic Acid In Guinea–Pigs: Effect Of Men 11467, A Selective Pseudopeptide Tachykinin NK–1 Antagonist.* Pharmacological Research—XXIX National Congress of Italian Pharmacological Society, Florence–Italy Jun. 20–23, 1999 Abstract Book, p. 90 (1999).

T.P. D. Fan et al. *Stimulation of angiogenesis by substance P and interleukin–1 in the rat and its inhibition by $NK_1$ or interleukin–1 receptor antagonists.* Br. J. Pharmacol. vol. 110, pp. 43–49 (1993).

T. A. Fregene et al. *Tumor—Associated Angiogenesis in Prostate Cancer.* Anticancer Research vol. 13, pp. 2377–2382 (1993).

T. Fujii et al. *Pharmacological profile of a high affinity dipeptide $NK_1$ receptor antagonist, FK888* Br. J. Pharmacol. vol. 107, pp. 785–789 (1992).

C. J. Gardner et al. *GR205171: A novel antagonist with high affinity for the tachykinin NK1 receptor, and potent broad–spectrum anti–emetic activity.* Regulatory Peptides vol. 65, pp. 45–53 (1996).

C. Garret et al. *Pharmacological properties of a potent and selective nonpeptide substance antagonist.* Proc. Natl. Acad. Sci. USA vol. 88, pp. 10208–10212 (Nov. 1991).

I. M. Hennig et al. *Substance–P Receptors In Human Primary Neoplasms: Tumoral and Vascular Localization.* Int. J. Cancer vol. 61, pp. 786–792 (1995).

B. V. Offersen et al. *Immunohistochemical determination of tumor angiogenesis measured by the maximal microvessel density in human prostate cancer.* APMIS vol. 106, pp. 463–469 (1998).

D. Regoli et al. *Receptors and Antagonists for Substance P and Related Peptides.* Pharmacological Reviews vol. 46, No. 4, pp. 551–559 (1994).

W. Schilling et al. *Approaches towards the Design and Synthesis of Nonpeptidic Substance–P Antagonists.* pp. 207–220.

R. M. Snider et al. *A Potent Nonpeptide Antagonist of the Substance P ($NK_1$) Receptor.* Science vol. 251, pp. 435–437 (Jan. 1991).

Primary Examiner—James H Reamer
(74) Attorney, Agent, or Firm—Morgan & Finnegan, L.L.P.

(57) ABSTRACT

It is described the use of antagonists of neuro kynin receptors (NK-1; substance P receptors) in order to establish a new drug effective in the treatment of adenocarcinomas, such antagonists being one or more substances selected among those ones having the following features: $pA_2 > 6.0$ both in human and in murine tissues, etherocyclic non peptidergic structures, antiangiogenic effects experimentally demonstrated onto the genito-urinary tract rumors induced via orthotopic drafts of human tumoral cells either in the genito-urinary apparatus of either immunodeficient rats or mice, decrease of the tumoral mass on tumors of the genito-urinary tract induced by orthotopic drafts of tumoral cells onto tissues of the genito-urinary tract of either immunodeficient rats or mice.

11 Claims, No Drawings

USE OF SUBSTANCE P ANTAGONISTS IN THE TREATMENT OF THE ADENOCARCINOMAS

FIELD OF INVENTION

The present invention refers to, the use of substance P antagonists particularly the invention refers to the use of NK-1 receptor antagonists for the treatment of adenocarcinomas, more particularly genito-urinary-tract neoplasms, more particularly prostatic carcinoma.

STATE OF THE ART

Malignant neoplasms, originating from epithelial cells are named carcinomas. A peculiar type of carcinoma, of glandular origin, is the adenocarcinomas. Since a correlation between tumors and angiogenesis has been hypothesized, a possible, effective strategy against cancer disease is a pharmacological treatment with angiogenesis inhibitors.

Angiogenesis, i.e. the formation and development of new capillary vessels, occurs in different physiologic conditions, such as embryonal development. On the other hand, intense angiogenesis occurs in several pathologic conditions, such as synovial rheumatoid hypertrophy, atherosclerosis, proliferative retinopathy and solid tumors. With reference to solid tumors, the interest in the neovascularisation has been raised from the evidence that tumors cannot growth or metastasize without new vessels and/or growth factors. Solid tumors cannot grow beyond 1–2 mm$^3$ without neovascularation, which furnishes feeding to tumors. Therefore, experiments have been carried out in order to quantify neovascularation in order to try to evaluate the tumor growth at different stages [Tosan A., Fregene et al, Anticancer Research 13: 2377–2382 (1993); 13: Brigitte V. Offersen et al., APMIS 106: 463–469 (1998)]. Consequently, it has been hypothesized that tumor growth could be prevented by neovascularization blockage.

Experimental evidences have recently outlined that substance P (SP) plays a role in angiogenesis stimulation:

- Daily administration of substance P causes intense neovascularization in a rat sponge model of angiogenesis [T.-P. D. Fan et al, Br. J. Pharmacol. 110: 43–49 (1993)];
- The angiogenic response towards SP can be blocked by using selective antagonists for NK-1 receptors for tachykinines [T.-P. D. Fan et al, Br. J. Pharmacol. 110: 43–49 (1993)];
- The angiogenic activity of SP can be counteracted by administration of either peptide or non peptide antagonists [D. Regoli et al., Pharmacol. Rev., Vol. 64, No. 4 551–559 (1994)].

EP 0835662 describes peptide antagonists of substance P which are characterized by negative side effects. Henning Ivo M. et al., Int. J. Cancer. 61, 786–792 (1995) describes binding experiments for substance P receptors and hypothesizes that the progression of tumor is mediated via angiogenetic mechanisms.

Such experimental results have not yet led to identify any drug which could be successfully employed in the treatment of the adenocarcinomas, particularly the prostatic carcinoma. As a matter of fact, Fan et al. states about future therapeutic applications in the above mentioned mechanism.

Moreover, NK-1 antagonists show a great variability in their molecular structure (Regoli et al, 1994), therefore being very difficult to predict potential activity based upon their structure-activity relationship. Also, insofar, no data have currently shown that the antagonistic activity and selectivity towards the human subtype NK-1 receptor could be of interest in the therapy of adenocarcinoma, particularly of the prostatic adenocarcinoma. In relation to the current state of the art regarding cancer therapy, none of the tested substances seems to be effective in cancer therapy. Therefore for the substances mentioned in Regoli it cannot be inferred any specific activity against cancer.

With the present invention, we aim at inhibiting, via administration of inhibitors of angiogenesis and particularly by using of antagonists of NK-1 tachykinergic receptor, solid tumor growth specifically localized to the genito-urinary tract. This innovative methodology either substitutes or integrates current therapies against cancer, such as surgery, chemiotherapy and radiotherapy.

SUMMARY OF THE INVENTION

It is an object of the present invention the use of NK-1 receptor antagonists in the treatment of the adenocarcinomas, particularly in the treatment of the carcinomas of the genito-urinary tract and more particularly in the treatment of the prostatic adenocarcinoma.

Another object of the invention is the use of substance P antagonists in the treatment of the adenocarcinomas, particularly in the treatment of the carcinomas of the genito-urinary tract and more particularly in the treatment of the prostatic adenocarcinoma.

Further objects of the invention will be evident by the following detailed description of the invention.

DETAILED DESCRIPTION OF THE INVENTION

The present invention refers to the use of substance P receptor antagonists particularly NK-1 receptor antagonists, in the treatment of adenocarcinomas, particularly genito-urinary tract neoplasms, more particularly prostatic carcinoma. Selected antagonists according to the present invention are listed in Tab. 1 and are characterised by the following features:

1) $pA_2 > 6.0$ both in murine and human tissues, $pA_2$ being the concentration of the drug at which it is half-maximally effective, and the $pA_2$ is directly related to the affinity of the ligand to the receptor,
2) Non peptidic heterocyclic structure.
3) Antiangiogenic effects experimentally evaluated onto tumors of the genito-urinary tract induced via orthotopic grafts of tumoral human cells on tissues of the genito-urinary tract of rats and/or immunodeficient mice. Orthotopic graft is intended to be a graft of cells in the host, via direct injection of cells.
4) Reduction of the tumoral mass experimentally demonstrated onto tumors of the genito-urinary tract induced via orthotopic grafts of tumoral human cells on tissues of the genito-urinary tract of rats and/or immunodeficient mice.

The following substances are considered by the authors effective against adenocarcinomas, specifically against the adenocarcinomas originating from the genito-urinary tract.

TABLE 1

| Compound | pA$_2$ human | pA$_2$ rat | References |
|---|---|---|---|
| FK 888 | 9.1 | 6.0 | Fujii et al., Br. J. Pharm. 107:785, 1992 |
| CP 96345 | 9.5 | 6.8 | Srider et al., Science 251:435, 1991 |
| CP 99994 | 8.9 | 6.1 | Desal et al., J. Med. Chem. 35:4911, 1992 |
| SR 140333 | 9.8 | 7.4 | Edmonts et al., Eur. J. Pharm. 250:403, 1993 |
| CGP 47899 | >6.0 | >6.0 | Shilling et al., Pers. Med. Chem. 207, 1993 |
| RP 67580 | 7.2 | 8.2 | Garret et al., PNAS 88:10208, 1991 |
| MEN 11149 | >6.0 | >6.0 | Cirillo et al., Eur. J. Pharm. 341:201, 1998 |
| MEN 11467 | >6.0 | >6.0 | Evangelista et al., XXIX Nat. Congr. of the Ital. Pharmacological Soc., Florence 20–23.06, 1999 |
| GR 205171 | >6.0 | >6.0 | Gardner et al., Regul Pep. 65:45, 1996 |
| L-703,606 | | | Cascieri et al., Mol. Pharmacol. 42, 458, 1992 |

The above mentioned substances may be used to prepare drugs in combination with known adjuvants. Sinergistically, they can be combined with substances listed in table 2. As a matter of fact, the combination of one or more substances listed in table 1 with one or more substances in table 2 (or corresponding derivatives of the substances listed in table 2, derivatives known to the man skilled in the art) provides a therapeutic positive response higher than 10%, as stated in points 3-4 of the pharmacological characteristics of the NK-1 antagonists.

TABLE 2

| | |
|---|---|
| FLUTAMIDE (Eulexin by Schering; Drogenil by Essex). | Preferred dose range: 15–1500 mg/day |
| LEUPROLIDE ACETATE (Enantone by Takeda). | Preferred dose range: 0.1–10 mg/month |
| GOSERELIN (Zoladex by Zeneca). | Preferred dose range: 0.1–10 mg/28 days |
| AMINOGLUTETHIMIDE (Orimeten by Ciba-Geigy). | Preferred dose range: 30–3000 mg/day |
| KETOKONAZOLE (Zinoral by Janssen). | Preferred dose range: 10–1000 mg/day |
| DOXORUBICINA (Adriblastina by Pharmacia & Upjohn). | Preferred dose range: 2–100 mg/day |
| TAXOL | Preferred dose range: 2–100 mg/day |

Route of administration is based upon the specific characteristics of the compounds and implies the endovenous, intrabladder, intraperitoneal, intramuscular, subcutaneous and oral administration.

Adjuvants are selected among those commonly used in pharmacotherapy, such as: methyl-p-hydroxybenzoate, latex and saline solution.

Administration of substances listed in table 1, possibly in combination with substances listed in Table 2, is able to either reduce or reverse tumor growth via inhibition of angiogenesis and tumoral mass.

Moreover, use of antagonists of substance P is endowed of the following advantages:

Antiemetic effect, opposite to chemiotherapic drugs which show marked emetic effects Antidepressive effect, which is a very important psychotherapic effect in cancer affected patients.

The following examples should be considered as illustrative of the present invention an not limitative of the scope of the invention itself.

MATERIALS AND METHODS

Animals

For this studies has been used male athymic nude mices (Harlan). The mices were housed in laminar flow cabinet under pathogenic free conditions and used at 4–5 weeks of age.

Orthotopic Implantation

The PC-3 human prostatic cancer cell lines (ECACC) were mantained in Minimum essential medium (GIBCO BRL) For in vivo studies, tumor cells in exponential growth phase were harvested by a 120 seconds treatment with tripsyn in 0.02% EDTA. After that the cells were resuspended in saline solution. 20 μl ($10^5$ cells) of saline solution was inoculated in nude mice prostate. The tumors were taken at different times (three up to 180 days) for analysis.

Treatments

Animals were divided in groups (10 animals each one) and treated with different solutions:
physiological solution, -Sustance P (1 ng up to 1 mg), -L-703,606 (1 ng up to 1 mg), -L-703,606+Leuprolide Acetate (using dosages reported in table 1 and 2).

The treatments were made at different time (one at day until one at week). For different periods of time (three days up to 180 days).

Immunohystochemistry

Frozen sections of tumors have been fixed in Acetone, acetone/chloroform, acetone.

The presence of new blood vessels has been highlighted using the Rat anti-Mouse CD31 antibody, a Goat anti-Rat POX as a secondary antibody and DAB as a chromogen substrate. For quantification of blood vessels an image analysis system was employed.

Cancerogenicity

The animals were maitained under observation for three up to 180 days. Autoptic examinations were performed in all animals and the tumoral mass weighed.

Results

Vascular Density Quantification

The quantitative data obtained on blood vessels density have shown a statistically significant difference ($p<0.05$) amongst different treatments. SP treated mice group showed a statistically significant increase of CD 31 values compared to control groups ($p<0.05$).

Moreover, a statistically significant reduction ($p<0.05$) of CD 31 values has been outlined in mice treated with L-703,606 compared either to control groups or SP treated mice. The inhibitory angiogenic effect mediated by L-703,606 has been shown in all groups treated with this compound. A statistically significant reduction of CD 31 values has been shown with L-703,606+Leuprolide, Acetate ($p<0.05$) compared to L-703,606 groups (>10%).

Tumoral Mass Weight

Tumoral mass weight has been evaluated in all experimental groups, throughout treatment days (from 3 up to 180 days). Results have shown a statistically significant reduction ($p<0.05$) of tumoral mass weight in mice treated with L-703,606, compared to either control groups or SP treated mice. Moreover, combination of L-703,606 with Leuprolide Acetate allows to reveal a further tumoral mass reduction, (>100%).

Correlation between tumoral mass weight and type of treatment is proportionally related to treatment time-course.

What is claimed is:

1. A method for treating adenocarcinomas comprising the steps of administering to a subject in need of treatment a pharmaceutically effective amount of an antagonists of NK-1 receptors, such antagonists being one or more compounds and corresponding mixtures selected among the compounds having the following characteristics:

$pA_2>6.0$ in human and murine tissue;

non peptidic heterocyclic structure;

antiangiogenetic effects experimentally demonstrated in urogenital tumors, induced by orthotopic implantation of human tumoral cells in immunodeficient rat and mice urogenital tissues, said orthotopic implantation being made by inoculating the rat and mice urogenital tissues with said human tumoral cells and said angiogenetig effects being measured by the reduction of tumoral mass in the urogenital tumors induced by the orthotopic implantation.

2. The method according to claim 1 wherein the compounds are selected among: FK 888, CP 96345, CP 99994, SR 140333, CGP 47899, RP 67580, MEN 11149, MEN 11467, GR 205171, L-703,606 and corresponding derivatives and corresponding mixtures.

3. The method according to claim 1 wherein the compound is combined with at least one compound selected among: FLUTAMIDE, LEUPROLIDE, GOSERELIN, AMINOGLUTETHIMIDE, KETOKONAZOLE, DOXORUBICINA, TAXOL and corresponding derivatives and corresponding mixtures.

4. The method according to claim 3 wherein each of the compounds is administered at the following dosage: FLUTAMIDE 15–1500 mg/day, LEUPROLIDE ACETATE 0.1–10 mg/month, GOSERELIN 0.1–10 mg/28 days, 30–3000 mg/day, 10–1000 mg/day, DOXORUBICINA 2–100 mg/day, TAXOL 2–100 mg/day.

5. The method according to claim 1 wherein the compounds are administered via endovenous, intrabladder, intraperitoneal, intramuscular, subcutaneous and oral route.

6. The method according to claim 1 wherein the compounds are mixed with adjuvants selected in the group consisting of: metil-p-hydroxybenzoate, latex, saline solution and corresponding mixtures.

7. The method according to claim 1, wherein the adenocarcinomas are urogenital adenocarcinomas.

8. The method according to claim 1, wherein the adenocarcinomas are prostatic adenocarcinomas.

9. A method to induce and test effects of NK-1 receptor antagonists in immunodeficient rat and mice urogenital tissues comprising the steps of: (i) making an orthotopic implantation by inoculating the mice and rat urogenital tissues with human tumoral cells, (ii) treating the tumoral cells after implantation with at least a compound, having $pA_2>6.0$ in human and murine tissue and non peptidic heterocyclic structure, for a period ranging between 3 to 180 days, and (iii) testing on frozen sections of tumors of the rat and mice the effect of the compound by measuring the tumoral mass reduction, said frozen section being taken where the inoculation has been made.

10. The method according to claim 9 wherein the human prostatic cells are the PC-3 human prostatic cancer cell lines.

11. The method according to claim 9 wherein the effect of the compound is tested by using Rat anti-Mouse CD31 antibody, Goat anti-Rat POX as a secondary antibody and DAB as a chromogen substrate.

* * * * *